(12) United States Patent
La Mendola

(10) Patent No.: US 6,520,495 B1
(45) Date of Patent: Feb. 18, 2003

(54) CLAMPING DEVICE WITH FLEXIBLE ARM

(76) Inventor: Christopher La Mendola, 418 W. Neck Rd., Lloyd Harbor, NY (US) 11743

( * ) Notice: Subject to any disclaimer, the term of this patent is extended or adjusted under 35 U.S.C. 154(b) by 0 days.

(21) Appl. No.: 10/056,539

(22) Filed: Jan. 24, 2002

(51) Int. Cl.[7] .................................................. B25B 1/20
(52) U.S. Cl. ................................ 269/45; 269/3; 269/6; 248/104; 248/229.13; 24/300; 24/543
(58) Field of Search .............................. 269/45, 257, 6, 269/3; 248/104, 229.13, 229.23, 231.51; 24/300, 482, 495, 543

(56) References Cited

U.S. PATENT DOCUMENTS

| | | | |
|---|---|---|---|
| 1,542,208 A | * 6/1925 | Berger ........................ | 24/489 |
| 2,324,803 A | 7/1943 | Snyder | |
| 2,510,198 A | 6/1950 | Tesmer | |
| 2,887,974 A | * 5/1959 | Weinfeld ..................... | 269/45 |
| 3,096,962 A | 7/1963 | Meijs | |
| 3,168,274 A | 2/1965 | Street | |
| 3,584,822 A | 6/1971 | Oram | |
| 3,858,578 A | 1/1975 | Milo | |
| 4,070,011 A | 1/1978 | Glesser | |
| 4,108,315 A | * 8/1978 | Inao ........................... | 211/124 |
| D293,470 S | 12/1987 | Adler | |
| 4,949,927 A | 8/1990 | Madocks et al. | |
| 5,348,259 A | 9/1994 | Blanco et al. | |
| 5,447,149 A | 9/1995 | Kikawada et al. | |
| 5,489,075 A | * 2/1996 | Ible ............................. | 248/104 |
| 5,626,607 A | 5/1997 | Malecki et al. | |
| 5,662,300 A | * 9/1997 | Michelson ............... | 248/279.1 |
| 5,899,425 A | 5/1999 | Corey, Jr. et al. | |
| 5,934,656 A | * 8/1999 | Carder ........................ | 269/43 |
| 6,119,906 A | * 9/2000 | Bond et al. .................. | 223/96 |
| 6,173,947 B1 | * 1/2001 | Johnson ...................... | 269/17 |
| 6,357,710 B1 | * 3/2002 | Fielden et al. ........... | 248/276.1 |

* cited by examiner

*Primary Examiner*—Lee Wilson
(74) *Attorney, Agent, or Firm*—Greenberg Traurig, LLP; Todd S. Sharinn

(57) ABSTRACT

An apparatus for clamping an object includes a clamp with a first gripping element and a second gripping element that is connected by a pivot rod and includes a resilient element to maintain the clamp in closed position in the absence of applied pressure, and a release mechanism. An arm with a cable encased by a plurality of tubular, cone shaped segments is attached to the release mechanism, which is in turn attached to the clamp and includes either coil springs or bow springs for maintaining tension in the cable when the clamp is in a closed position, and for releasing tension in the cable when the clamp is opened.

40 Claims, 12 Drawing Sheets

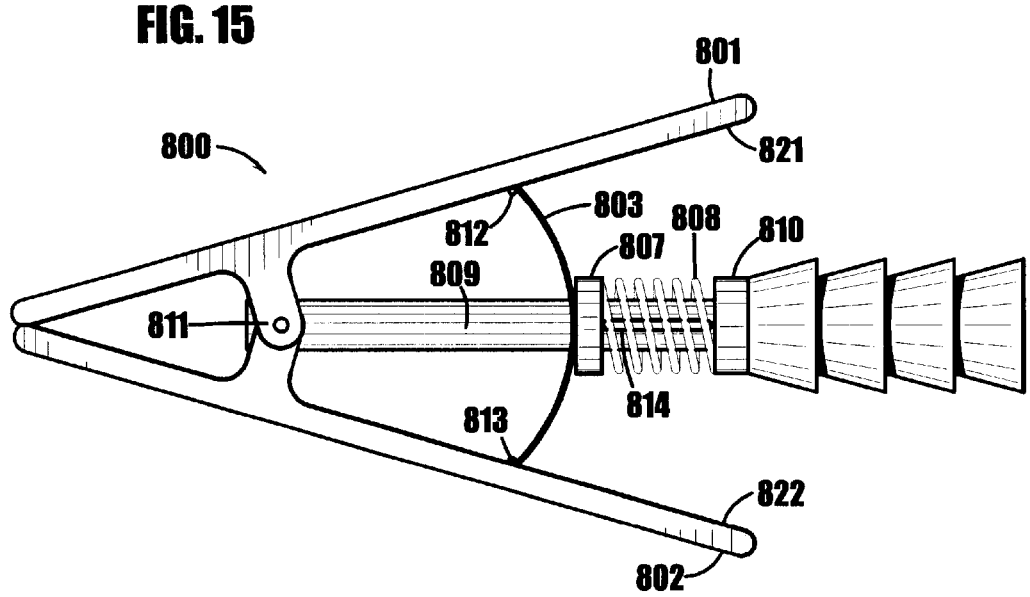

CLAMPING DEVICE WITH FLEXIBLE ARM

FIELD OF THE INVENTION

This invention is directed to a clamping device with an attached arm in which the act of opening the clamp makes the arm flexible and closing the clamp makes the arm rigid. The arm can be made flexible independently of opening the clamp.

BACKGROUND OF THE INVENTION

Clamping devices are well known in the mechanical arts, being useful for work projects such as carpentry, plumbing, electronics, auto repair, and surgery. Many such clamping devices are attached to flexible arms, as described in, for example, U.S. Pat. Nos. 2,510,198, 2,887,974, and 3,858,578. However, none of these clamping devices enables a user to clamp an object safely and independently and make rigid the flexible arm with one motion. Each requires that the flexible arm be positioned and then held in place to clamp a workpiece while a separate mechanism is used to render the arm rigid.

Each of the prior art clamping devices has the disadvantage that a user must in separate motions clamp a workpiece and then position the arm of the clamp, thus making it difficult to properly position a workpiece. In these situations, many adjustments are frequently necessary before a workpiece is properly positioned and clamped. Thus, there is a need for a clamp with an attached flexible arm wherein the arm can be made rigid in the same movement that closes the clamp.

SUMMARY OF THE INVENTION

This invention in one embodiment is a device that includes a simple spring clamp connected to a segmented arm that can be made rigid and immobile by releasing hand pressure on the clamp. Application of hand pressure to the clamp makes the clamp open and the arm flexible, thereby allowing it to be easily repositioned. The clamping device of the invention includes a central anchoring point with a release that enables a user to render the arm flexible without opening the clamp and releasing the workpiece. The uses of such a device are numerous, including many mechanical work projects such as carpentry, plumbing, auto repair and surgery.

In one embodiment, the device includes two clamps and two arms each meeting at a central anchoring point, which would also have an independent mechanism for making the arms flexible. One clamp could be affixed to a stationary object and the other clamp could be used to hold a workpiece and move it into any of an essentially infinite number of desirable positions before making the arms rigid. Once in position, the user may easily return the arms to their rigid state, holding the workpiece in a steady, convenient location.

In other embodiments the device could include any number of flexible arms connected together by a common central anchoring point to create a spiderlike device useful for holding multiple workpieces or the same workpiece in multiple locations. Each flexible arm can be connected to any of a variety of clamping devices. In another modification, a portable stand could be connected to the central anchoring point to allow the device to be freestanding.

The importance of this device is that it allows a worker to hold a workpiece in any number of different and easily attainable positions while still securing the piece and immobilizing the arm in a single step.

BRIEF DESCRIPTION OF THE DRAWINGS

FIG. 15 is a side view of a fifth embodiment of the bow spring clamp of the invention.

DETAILED DESCRIPTION OF THE INVENTION

Figure 1:
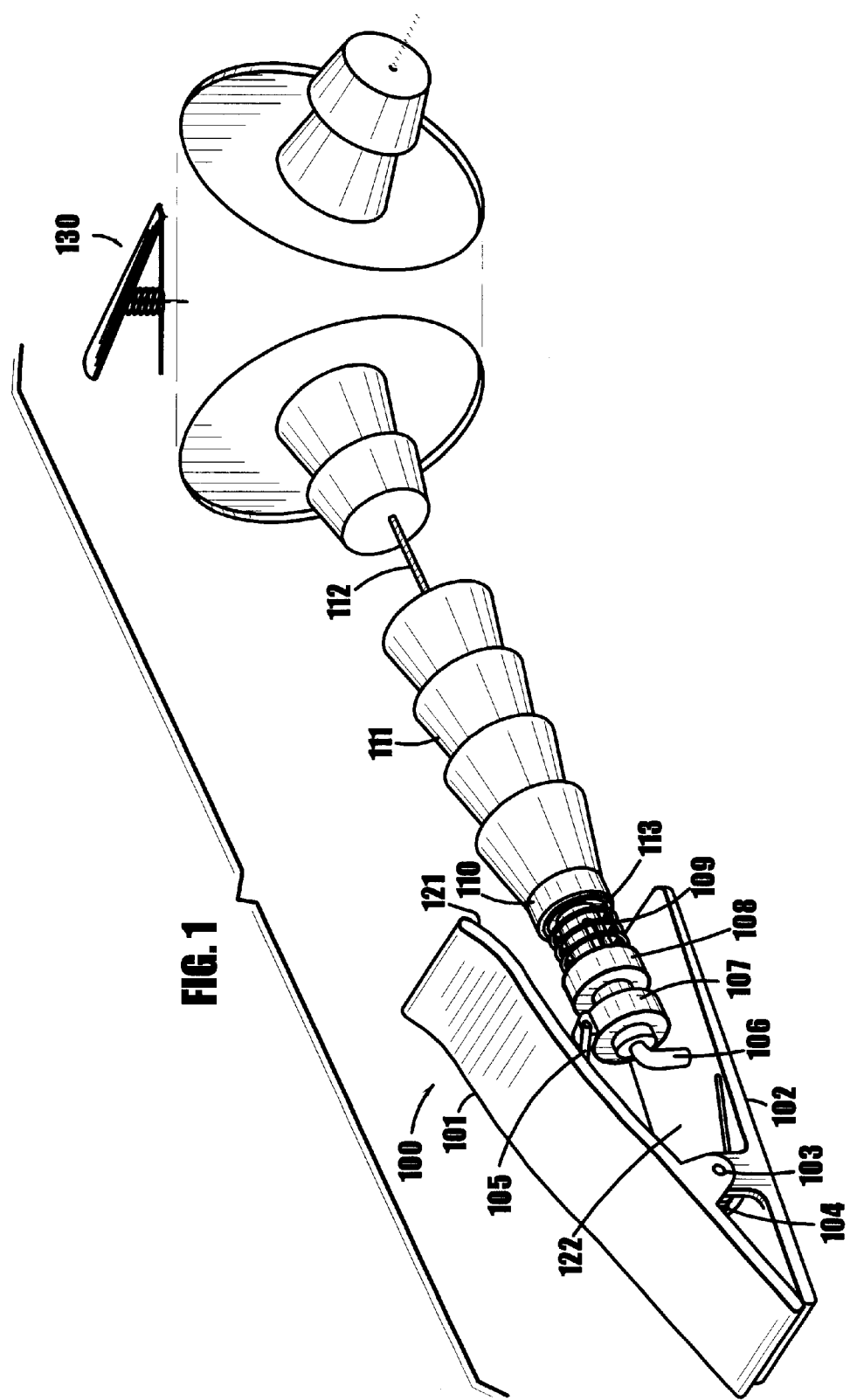
FIG. 1 is a perspective view of one variation of a coil spring clap embodiment of the invention.

FIG. 1 depicts a perspective view of a first preferred embodiment of a coil spring clamp 100 of the invention. The clamp of this embodiment includes a first gripping element or handle 101 and a second gripping element or handle 102 connected by a center pivot rod 103. A resilient element such as a pivot spring 104 encircling pivot rod 103 serves to maintain the clamp in a closed position as shown, until pressure is applied to the handles 101 and 102. The first handle 101 has an underside 121 that faces an underside 122 of second handle 102.

The clamp attaches to an arm encasing a cable or wire. One embodiment of such an arm includes a cable 112 encased in a plurality of short, tubular cone-shaped segments 111 which terminate at a fixed anchor ring 110 that is attached to the underside 122 of second handle 102. The cable 112 of the invention can be manufactured from a metallic, plastic, or any other suitable material. The cable 112 need not have a solid cross section, and can be hollow. Each tubular cone-shaped segment 111 is open at a wide end and closed at a narrow end, with the closed end being penetrated by a bore at the center through which the cable 112 can pass.

Figure 2A:
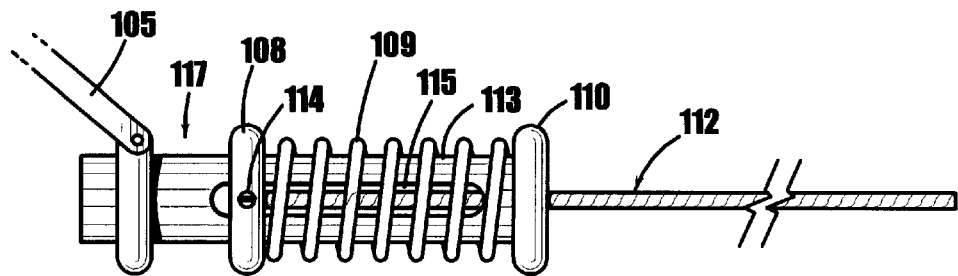
FIG. 2a is a detailed side view of the spring mechanism of the clamp depicted in FIG. 1.
Figure 2B:
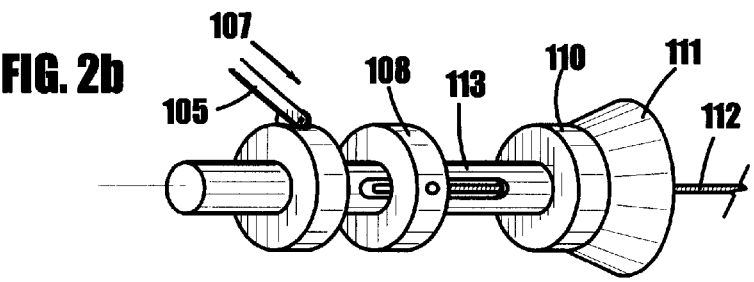
FIG. 2b is a perspective view of the mechanism of FIG. 2a with the spring removed.
Figure 2C:
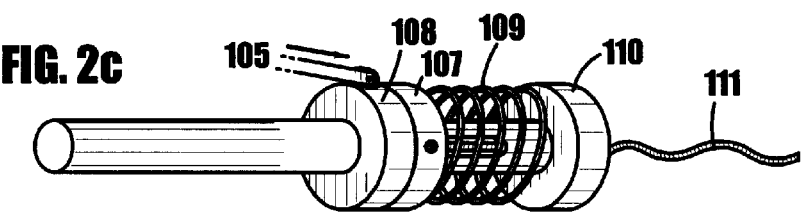
FIG. 2c is a perspective view of the mechanism of FIG. 2a depicting the two rings in an engaged position compressing the spring.
Figure 2D:
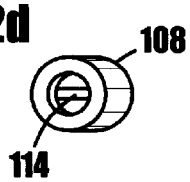
FIG. 2d is a perspective view of a sliding ring with an anchor pin.

Attached between the fixed anchor ring 110 and a fixed anchor point 106 that is also attached to the underside 122 of second handle 102 is a hollow grooved tube 113. The cable 112 continues through an opening in fixed anchor ring 110 into the hollow, grooved tube 113 and connects to first sliding ring 108. As shown in FIG. 2a, the first sliding ring 108 is disposed so that it encircles hollow grooved tube 113, and includes an anchor pin 114 that extends laterally through the groove 115 of hollow grooved tube 113. A view of first sliding ring with the anchor pin is depicted in FIG. 2d. Cable 112 attaches to anchor pin 114. A coil spring 109 serves to separate first sliding ring 108 from fixed anchor ring 110.

Referring again to FIG. 1, pivotally connected to the underside 121 of first handle 101 is a connecting arm 105, which is also pivotally connected to a second sliding ring 107 disposed to encircle hollow grooved tube 113. When the handles 101 and 102 are not under pressure, the clamp is closed, there is a space 117 between second sliding ring 107 and first sliding ring 108, and spring 109 maintains a separation between first sliding ring 108 and fixed anchor ring 110. By so doing, the coil spring 109 places the cable 112 under tension, causing axial compression of the tubular cone-shaped segments 111 against each other causing the arm of device 100 to remain in a rigid, fixed position.

When pressure is applied to the handles 101 and 102, the clamp begins to open, lever arm 105 slides so as to cause second sliding ring 107 to move towards first sliding ring 108, closing space 117. The movement of second sliding ring 107 towards first sliding ring 108 is depicted in FIG. 2b. As pressure continues to be applied to the handles 101 and 102, second sliding ring 107 engages first sliding ring 108 and moves it towards fixed anchor ring 110, compressing coil spring 109, which in turn relieves the tension on cable 112, causing it to go slack, a process depicted in FIG. 2c. This enables the tubular cone-shaped segments 111 to separate and the arm to become flexible. The existence of the space 117 allows the clamp handles to be closed a certain amount without losing the rigidity of the arm. This allows a user to clamp or unclamp on object without necessarily causing movement of the arm. One must squeeze the handles 101 and 102 almost fully to cause the arm to become flexible.

Figure 10:
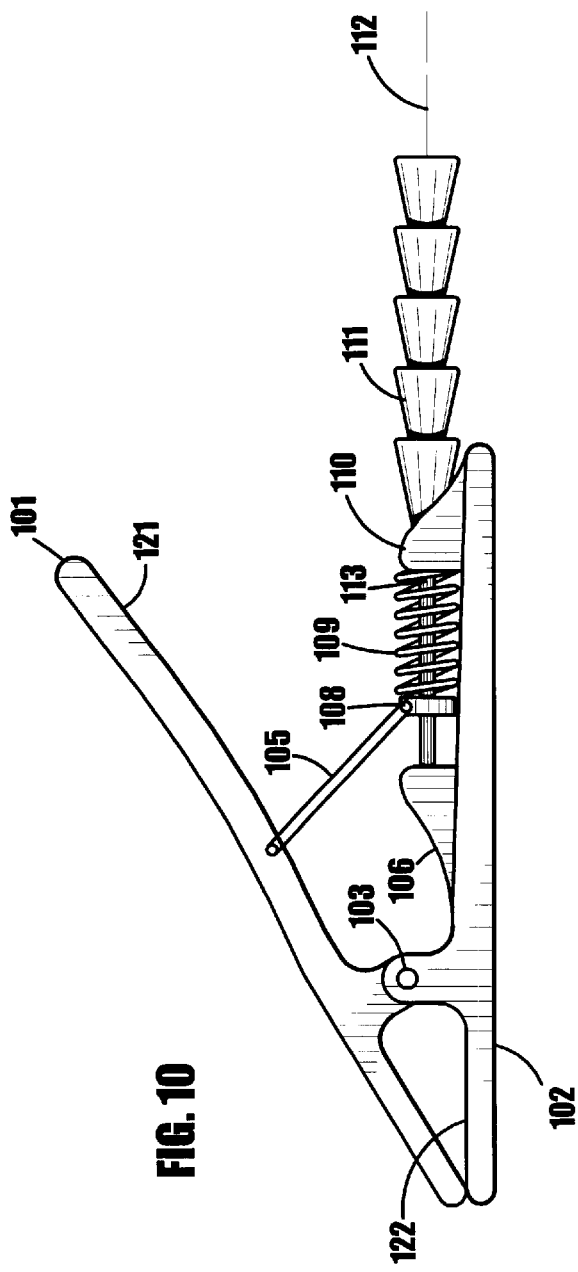
FIG. 10 is a perspective view of a third variation of a coil spring clap embodiment of the invention.

A less preferred embodiment utilizing only one sliding ring and thus lacking the space is depicted in FIG. 10. In this embodiment, lever arm 105 connects directly to first sliding ring 108. Application of pressure to handles 101, 102 causes lever arm 105 to move sliding ring 108 towards fixed anchor ring 110, compressing coil spring 109, relieving tension on cable 112 thus rendering the arm flexible. However, in this embodiment, the arm will loose its rigidity as a user opens the clamp.

Figure 7:
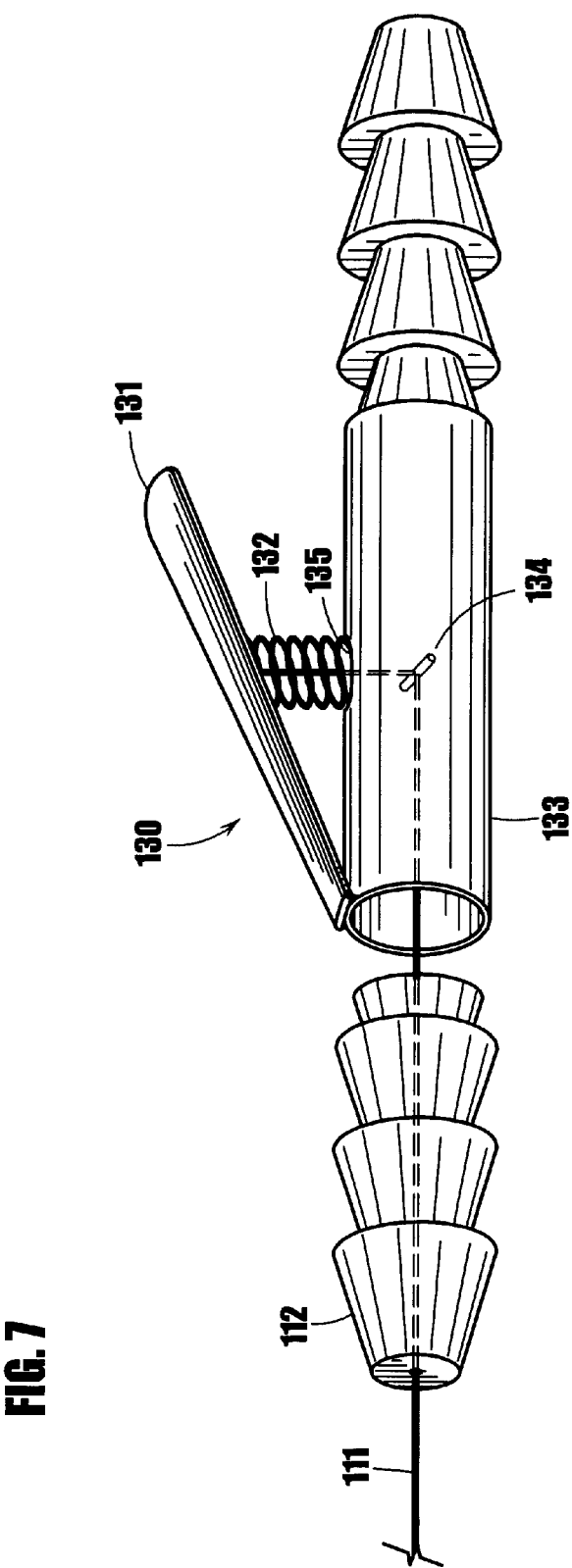
FIG. 7 is a perspective view of central anchoring point of the invention.

At the end of the flexible arm opposite of the clamp is a central anchoring point 130. The central anchoring point 130 is depicted in greater detail in FIG. 7. The tubular cone-shaped segments 111 encasing cable 112 terminate at a hollow cylindrical segment 133, which also encases the cable 112. In one embodiment of the central anchor point 130, cable 112 turns on a turning rod 134 attached on the inside of the cylindrical segment 133, emerges through opening 135 and is attached to lever arm 131. One end of lever arm 131 is hingedly attached to cylindrical segment 133, while the other end is held apart from the cylindrical segment 133 by spring 132, which also serves to maintain the tension on cable 112. Compressing lever arm 131 relieves the tension on cable 112, causing the arm to become flexible without releasing the object held by the clamp. This allows the arm to be mobile, independent of the clamp.

Figure 8A:
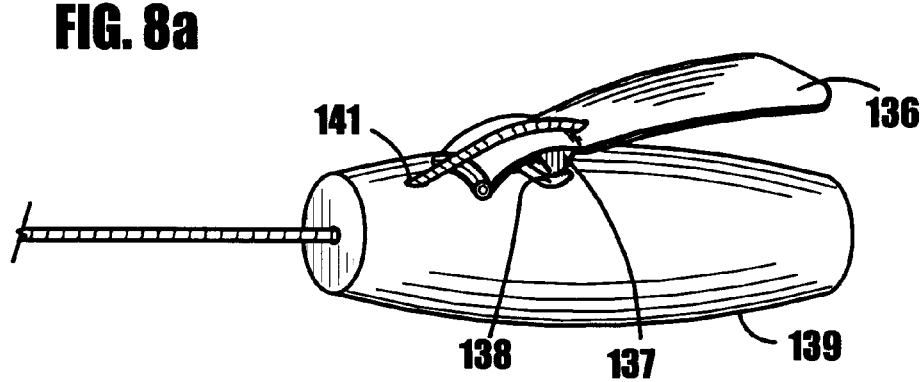
FIG. 8a depicts another variation of the central anchoring point of the invention in a locked position.
Figure 8B:
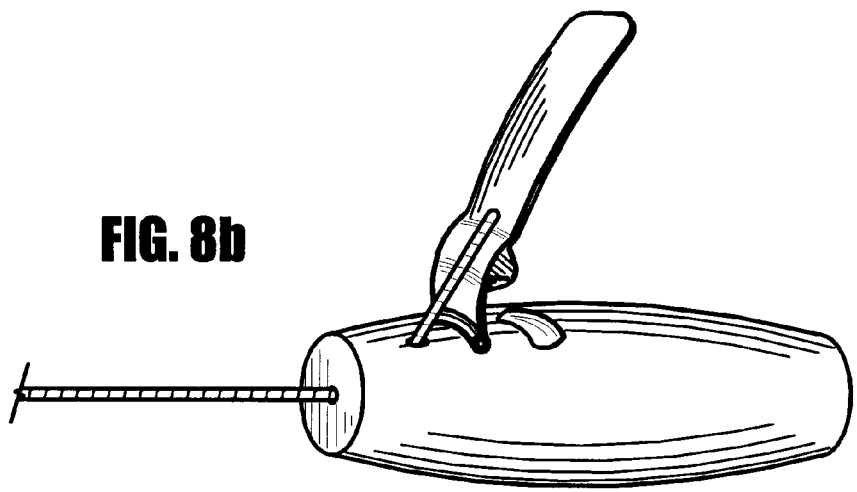
FIG. 8b depicts the central anchoring point of FIG. 8a in an unlocked position.

Another variation of the central anchor point 130 is depicted in FIGS. 8a and 8b. This variation includes a solid cylindrical segment 139. The cable 112 is threaded through a bore in the cylindrical segment 139, emerging at opening 141 and attaching to toggle arm 136. Toggle arm 136, which is also hingedly attached at one end to cylindrical segment 139 has a protuberance 137 near the attached end on the side opposite where cable 112 is attached. This protuberance 137 is shaped to fit into a depression 138 on the side of cylindrical segment 139 when the toggle arm 136 is moved to a closed, locked position, as shown in FIG. 8a. When the toggle arm 136 is locked, applying tension to cable 112, protuberance 136 will hold the toggle arm 136 in that position until unlocked by a user. FIG. 8b shows the toggle arm 136 in an open, unlocked position, relieving tension on cable 112.

Figure 8C:
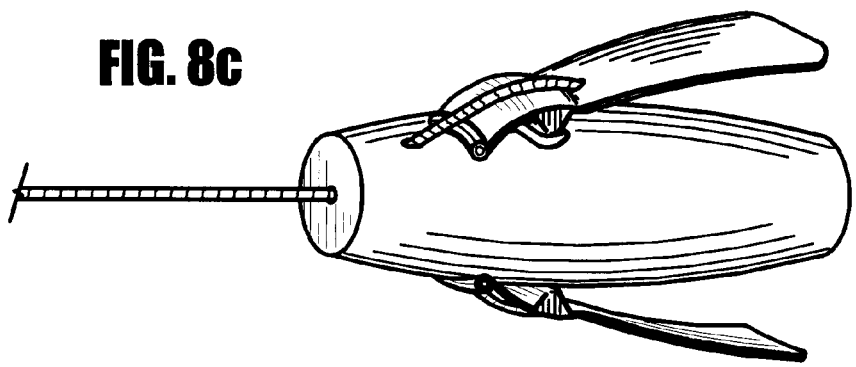
FIG. 8c depicts a dual central anchoring point.
Figure 9:
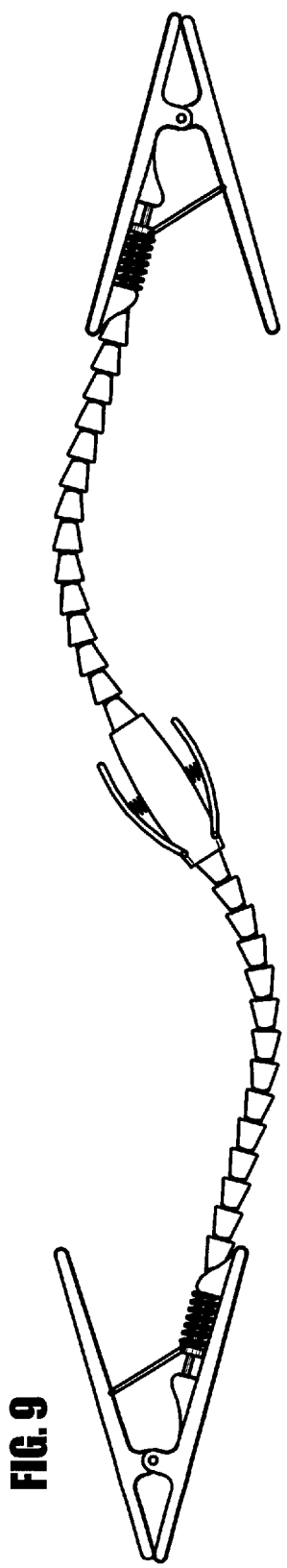
FIG. 9 is a side view of two springs clamp embodiments of the invention connected to a common central anchoring point.

FIG. 8c depicts another variation of the central anchor point 130 that is connected to two flexible arms, with toggle arms for each flexible arm disposed on opposite sides of the anchor point. A top view of two flexible arms attached to a common central anchor point is shown in FIG. 9. The central anchor point 130 can be fixed to a supporting or stationary object, such as a table-top or a wall.

Figure 3:
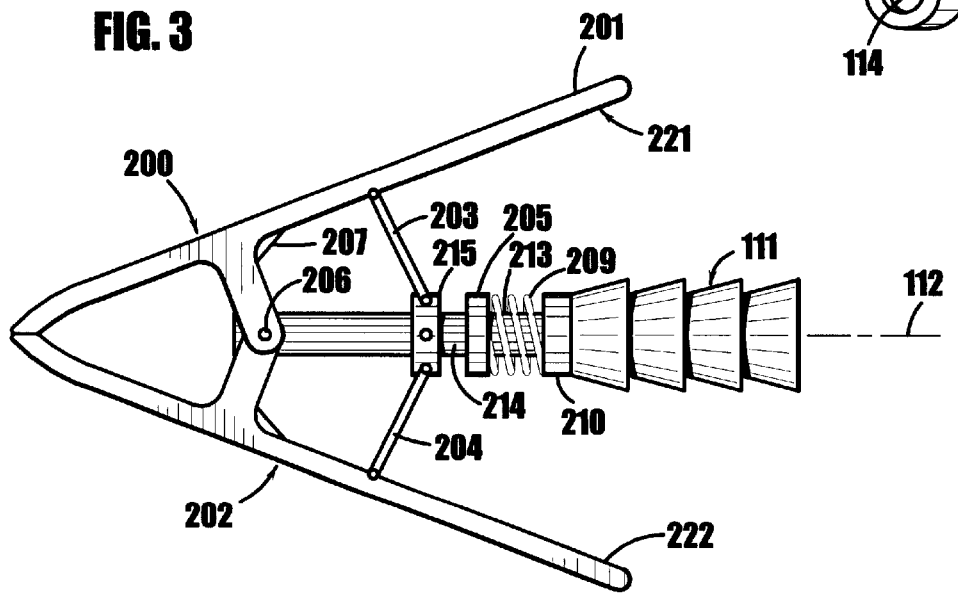
FIG. 3 is a perspective view of a second variation of the spring clap embodiment of the invention.

Other preferred embodiments of the clamping device of the invention are possible. FIG. 3 depicts a second embodiment of the coil spring clamp. The clamp 200 of this embodiment includes a first handle 201 and a second handle 202 connected by a center pivot rod 206. A resilient element such as a pivot spring 207 encircling pivot rod 206 serves to maintain the clamp in a closed position as shown until pressure is applied to the handles 201 and 202. The first handle 201 has an underside 221 that faces an underside 222 of second handle 202.

Attached to the center pivot rod 206 is one end of a hollow, grooved tube 213. Attached to the other end of hollow, grooved tube 213 is a terminating ring 210 that serves as a terminus for the tubular cone-shaped segments 111 encasing cable 112. A first sliding ring 205 encircles hollow, grooved tube 213, and includes an anchor pin (not shown) that extends laterally through groove 211 of hollow grooved tube 213. The cable 112 continues through an opening in the terminating ring 210 and through the hollow, grooved tube 213 to be attached to the anchor pin of sliding ring 205. A coil spring 209 serves to separate first sliding ring 205 from terminating ring 210. In addition, disposed upon hollow, grooved tube 213 between the first sliding ring 205 on the pivot rod 206 is a second sliding ring 215.

Pivotally connected to the underside 221 of first handle 201 is a first connecting arm 203, the other end of which is pivotally connected to second sliding ring 215. Similarly, pivotally connected to the underside 222 of second handle 202 is a second connecting arm 204, which is also pivotally connected to second sliding ring 215. When the handles 201 and 202 are not under pressure, the clamp is closed and there is a space 214 between first sliding ring 205 and second sliding ring 215, and spring 209 maintains a separation between first sliding ring 205 and terminating ring 210. By so doing, the coil spring 209 places the cable 112 under tension, causing axial compression of the tubular cone-shaped segments 111 against each other causing the arm of device 200 to remain in a rigid, fixed position.

When pressure is applied to the handles 201 and 202, the clamp begins to open, lever arms 203 and 204 move so as to cause second sliding ring 215 to move towards first sliding ring 205. As pressure continues to be applied to the handles 201 and 202, second sliding ring 215 engages first sliding ring 205 and moves it towards fixed anchor ring 210, compressing coil spring 209, which in turn relieves the tension on cable 112, causing it to go slack. This enables the tubular cone-shaped segments 111 to separate and the arm to become flexible.

Figure 12:
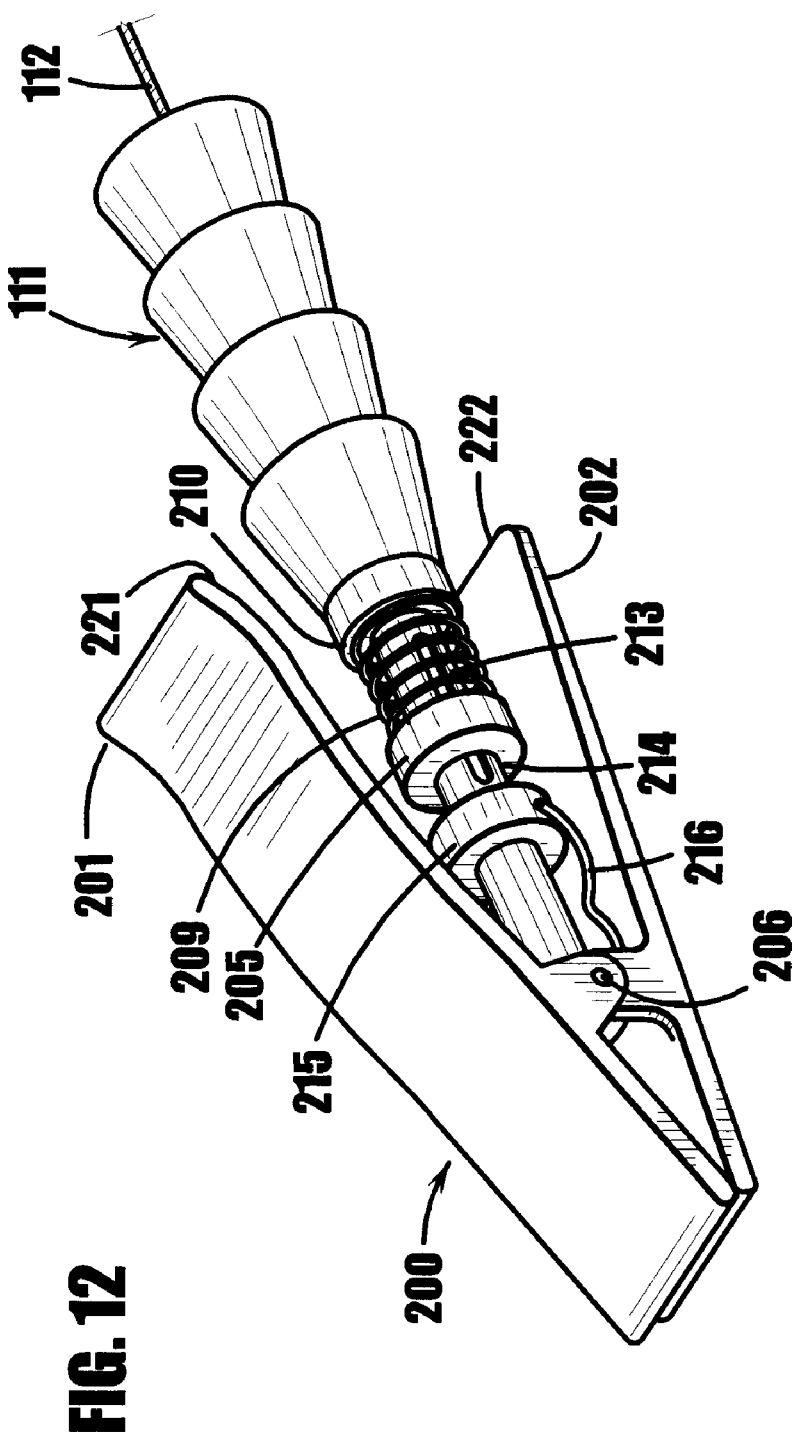
FIG. 12 is a perspective view of a fifth variation of a coil spring clap embodiment of the invention.

A variation of this embodiment utilizing only one lever arm is depicted in FIG. 12. In this embodiment, a horseshoe lever arm 216 replaces lever arms 203 and 204. The horseshoe lever arm connects one of the handles to the second sliding ring 215. Alternatively, the single horseshoe lever arm could be replaced by two separate lever arms wherein both lever arm connect to the underside of the same gripping element. Although FIG. 12 depicts the second handle 202 as being connected to the second sliding ring, the connection can easily be to the first handle 201. Again, application of pressure to handles 201 and 202 causes the horseshoe lever arm 216 to move second sliding ring 215 to engage first sliding ring 205 towards fixed anchor ring 210, compressing coil spring 209, relieving tension on cable 112 thus rendering the arm flexible.

Figure 11:
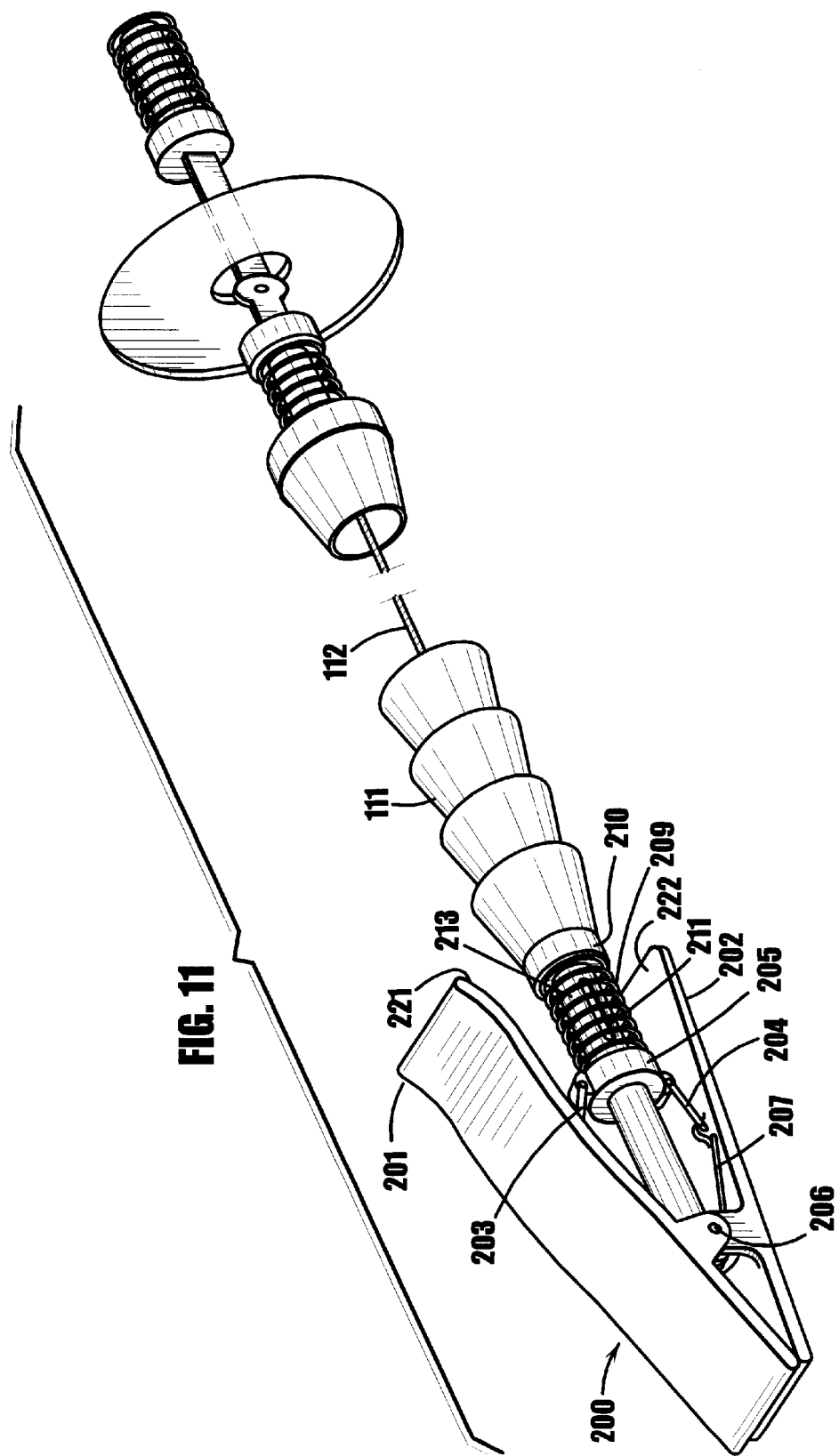
FIG. 11 is a perspective view of a fourth variation of a coil spring clap embodiment of the invention.

As with the case of the first coil spring embodiment, there is a less preferred embodiment, depicted in FIG. 11, that utilizes only one sliding ring and thus lacks the space between the first and second sliding rings. In this embodiment, lever arms 203 and 204 connect directly to the first sliding ring 205. Application of pressure to handles 201 and 202 causes lever arms 203 and 204 to move sliding ring 205 towards fixed anchor ring 210, compressing coil spring 209, relieving tension on cable 112 thus rendering the arm flexible. However, in this embodiment, the arm will loose its rigidity as a user opens the clamp.

Figure 4A:
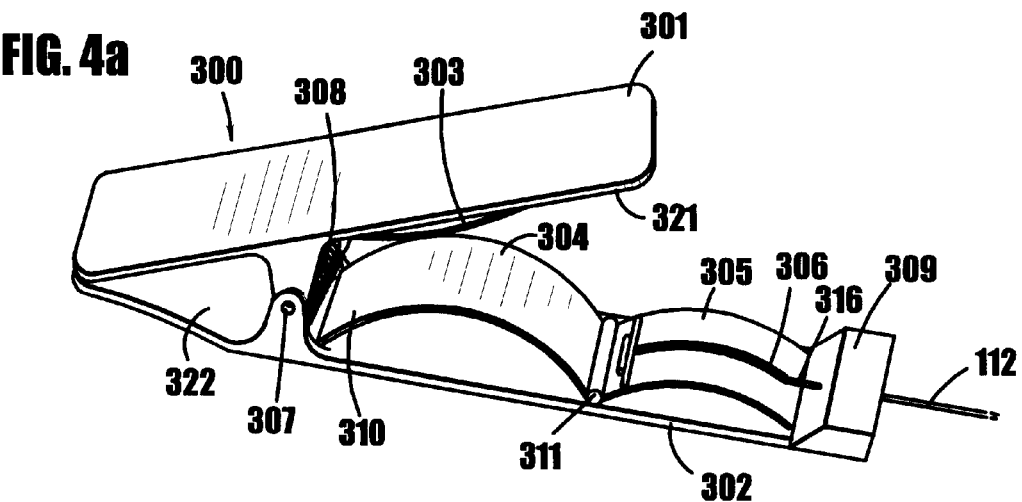
FIG. 4a is a perspective view of a bow spring clap embodiment of the invention.
Figure 4B:
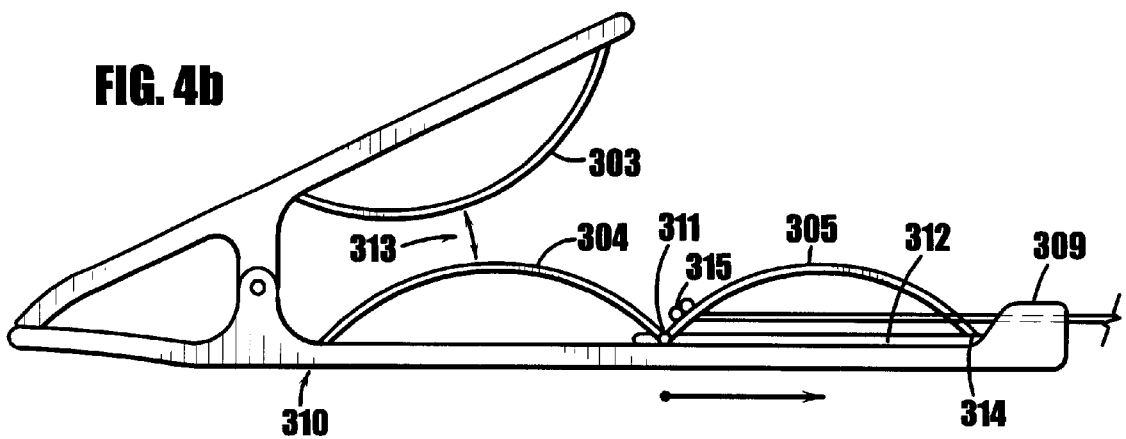
FIG. 4b is a side view of the clamp of FIG. 4a in an open position.

FIGS. 4a and 4b depict a bow spring embodiment of the clamp of the invention. The clamp 300 of this embodiment includes a first handle 301 and a second handle 302 connected by a center pivot rod 307. A resilient element such as a pivot spring 308 encircling pivot rod 307 serves to maintain the clamp in a closed position as shown until pressure is applied to the handles 301 and 302. The first handle 301 has an underside 321 that faces an underside 322 of second handle 302. At the end of the second handle 302 opposite the center pivot rod 307 is a raised knob 309 that serves as a terminus for the tubular cone-shaped segments 111, not shown in this figure for clarity. The raised knob 309 has a bore 316 through which the cable 112 passes.

Attached to the underside 321 of first handle 301 is a first bow spring 303. This first handle 303 is fixed at both ends and thus has little ability to flex. Attached to the underside 322 of second handle 302 is a second bow spring 304. One end 310 of second bow spring 304 is fixed to the underside 322 of second handle 302 proximal to the center pivot rod 307, while the other end is connected at a sliding connecting point 311 to a third bow spring 305. The sliding connecting point 311 slides in a track 312 that is recessed in the underside 322 of second handle 302.

Figure 4C:
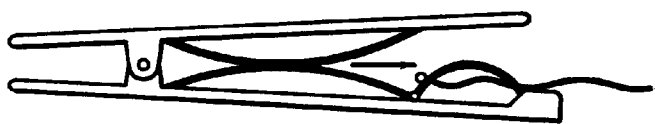
FIG. 4c is a side view of the clamp of FIG. 4a in a closed position.

The third bow spring is fixed at fixed end 314 to the raised knob 309, and includes a groove 306 through which the cable 112 can pass. The cable is fixed to the third bow spring 306 at anchor point 315. When pressure is applied to the handles 301 and 302, first bow spring 303 comes into contact with second bow spring 304 and depresses it, causing the sliding connecting point 311 to slide in track 312 towards fixed end 314. This releases tension on cable 112, allowing it to loosen and to make the arm flexible, as shown in FIG. 4c. Release of pressure reverses the process and causes the cable to tighten to make the arm rigid.

The degree of compression required to loosen the arm and the magnitude of the space 313 can be adjusted by a simple screw mechanism similar to the adjustment used on the handbrakes of a bicycle.

Figure 5:
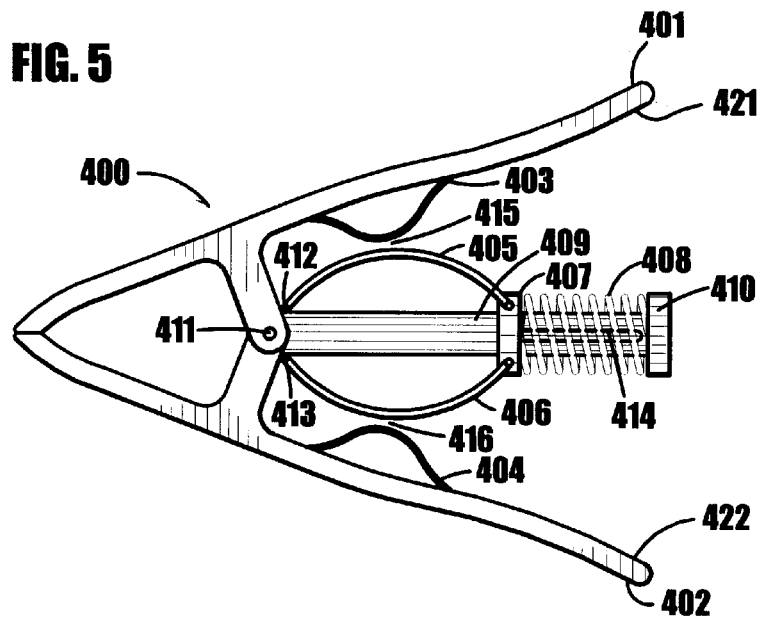
FIG. 5 is a side view of a second bow spring clap embodiment of the invention.

A second variation of the bow spring embodiment of the clamp is depicted in FIG. 5. The clamp 400 of this embodiment includes a first handle 401 and a second handle 402 connected by a center pivot rod 411. A resilient element, not shown for clarity, encircles the center pivot rod 411 and serves to maintain the clamp in a closed position as shown until pressure is applied to the handles 401 and 402. The first handle 401 has an underside 421 that faces an underside 422 of second handle 402.

Attached to the underside 421 of first handle 401 is a first bow spring 403, fixed at both ends to limit its ability to flex. Similarly, attached to the underside 422 of second handle 402 is a second bow spring 404, also fixed at both ends to limit its ability to flex. Attached to the center pivot rod 411 of the clamp is one end of a hollow grooved tube 409. On the other end of the hollow grooved tube 409 opposite of the center pivot rod 411 is a flange or terminating ring 410 that serves as a terminus for the tubular cone-shaped segments 111, not shown in this figure for clarity.

A sliding ring 407 encircles hollow, grooved tube 409, and includes an anchor pin (not shown) that extends laterally through groove 414 of hollow grooved tube 409. The cable, not shown for clarity, continues through the hollow, grooved tube 409 to be attached to the anchor pin of sliding ring 407. A coil spring 408 serves to separate sliding ring 407 from terminating ring 410.

Attached to the hollow grooved tube 409 on a side opposite the first bow spring 403 is a first flexible bow spring 405. One end of the first flexible bow spring 405 is fixed to the hollow grooved tube 409 at a point 412 proximal to the center pivot rod 411, whereas the other end of the first flexible bow spring 405 is attached to sliding ring 407. Similarly, attached to the hollow grooved tube 409 on a side opposite the second bow spring 404 is a second flexible bow spring 406. One end of the second flexible bow spring 406 is fixed to the hollow grooved tube 409 at a point 413 proximal to the center pivot rod 411, whereas the other end of the second flexible bow spring 406 is attached to sliding ring 407.

When pressure is applied to the handles 401 and 402, first bow spring 403 comes into contact with first flexible bow spring 404, while second bow spring 404 comes into contact with second flexible bow spring 406. The pressure applied by bow springs 403 and 404, respectively, to flexible bow springs 405 and 406 causes the flexible springs 405 and 406 to be depressed, causing the sliding ring 407 to slide in groove 414 towards terminating ring 410, compressing spring 408. This releases tension on the cable, allowing it to loosen and to make the arm flexible. Release of pressure reverses the process and causes the cable to tighten to make the arm rigid.

As with the first bow spring embodiment, the degree of compression required to loosen the arm and the magnitude of the spaces 415 and 416 can be adjusted by a simple screw mechanism similar to the adjustment used on the handbrakes of a bicycle.

Figure 13A:
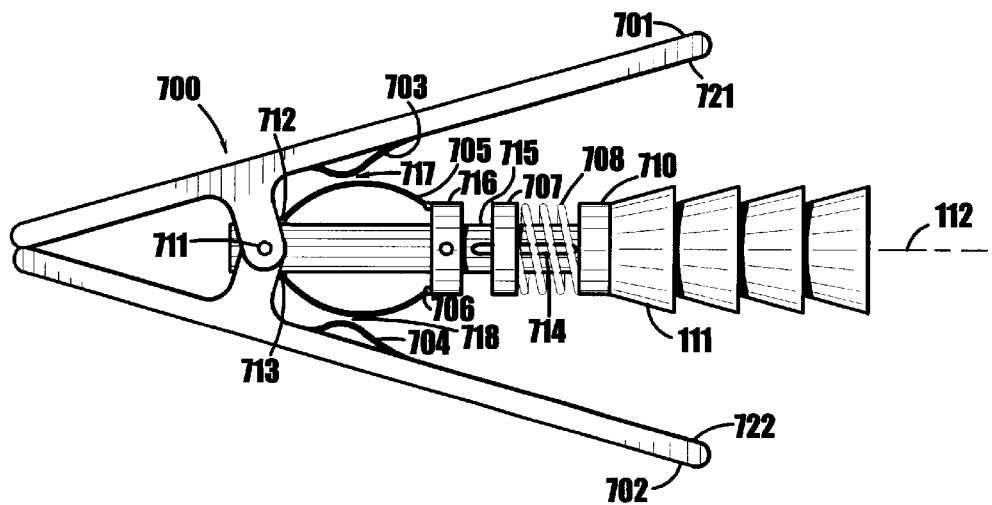
FIG. 13a side view of a third bow spring embodiment of the invention in an open position.
Figure 13B:
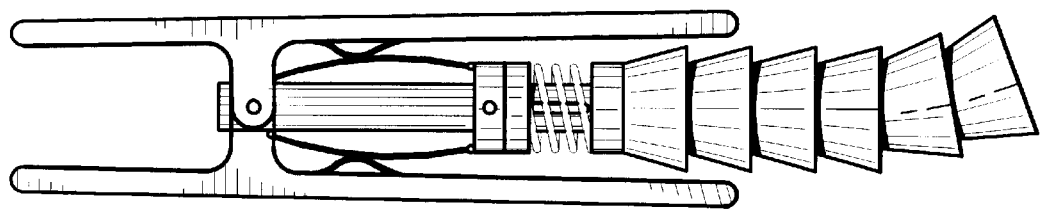
FIG. 13b side view of a third bow spring embodiment of the invention in a closed position.

A third variation of the bow spring embodiment of the clamp is depicted in FIG. 13. The clamp 700 of this embodiment includes a first handle 701 and a second handle 702 connected by a center pivot rod 711. A resilient element, not shown for clarity, encircles the center pivot rod 711 and serves to maintain the clamp in a closed position as shown until pressure is applied to the handles 701 and 702. The first handle 701 has an underside 721 that faces an underside 722 of second handle 702.

Attached to the underside 721 of first handle 401 is a first bow spring 703, fixed at both ends to limit its ability to flex. Similarly, attached to the underside 722 of second handle 702 is a second bow spring 704, also fixed at both ends to limit its ability to flex. Attached to the center pivot rod 711 of the clamp is one end of a hollow grooved tube 709. On the other end of the hollow grooved tube 709 opposite of the center pivot rod 711 is a flange or terminating ring 710 that serves as a terminus for the tubular cone-shaped segments 111.

A first sliding ring 707 encircles hollow grooved tube 709, and includes an anchor pin (not shown) that extends laterally through groove 714 of hollow grooved tube 709. The cable 112, continues through the hollow grooved tube 709 to be attached to the anchor pin of first sliding ring 707. A coil spring 708 serves to separate first sliding ring 707 from terminating ring 710. Disposed on hollow grooved tube 709 between first sliding ring 707 and the center pivot rod 711 is a second sliding ring 716.

Attached to the hollow grooved tube 709 on a side opposite the first bow spring 703 is a first flexible bow spring 705. One end of the first flexible bow spring 705 is fixed to the hollow grooved tube 709 at a point 712 proximal to the center pivot rod 711, whereas the other end of the first flexible bow spring 405 is attached to second sliding ring 716. Similarly, attached to the hollow grooved tube 709 on a side opposite the second bow spring 704 is a second flexible bow spring 706. One end of the second flexible bow spring 706 is fixed to the hollow grooved tube 709 at a point 713 proximal to the center pivot rod 711, whereas the other end of the second flexible bow spring 706 is attached to second sliding ring 716. In the absence of pressure applied to the handles 710 and 702, there is a space 715 between second sliding ring 716 and first sliding ring 707.

When pressure is applied to the handles 701 and 702, first bow spring 703 comes into contact with first flexible bow spring 704, while second bow spring 704 comes into contact with second flexible bow spring 706. The pressure applied by bow springs 703 and 704, respectively, to flexible bow springs 705 and 706 causes the flexible springs 705 and 706 to be depressed, causing the second sliding ring 716 to move so as to close space 715 and engage first sliding ring 707, causing it to slide in groove 714 towards terminating ring 710, compressing spring 708. This releases tension on the cable 112, allowing it to loosen and to make the arm flexible. Release of pressure reverses the process and causes the cable to tighten to make the arm rigid.

As with the first bow spring embodiment, the degree of compression required to loosen the arm and the magnitude of the spaces 717 and 718 can be adjusted by a simple screw mechanism similar to the adjustment used on the handbrakes of a bicycle.

Figure 14A:
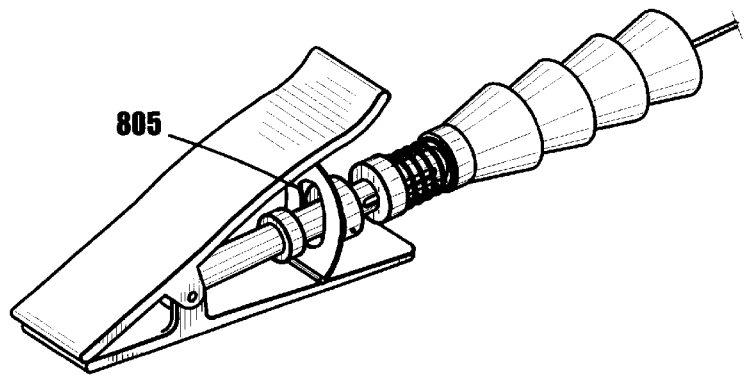
FIG. 14a perspective view of a fourth bow spring embodiment of the invention.
Figure 14B:
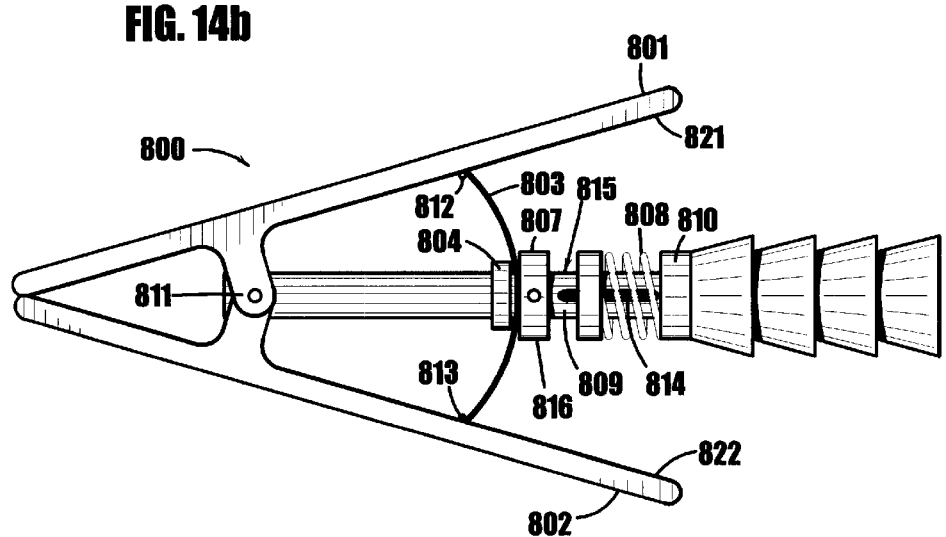
FIG. 14b side view of a fourth bow spring embodiment of the invention in an open position.
Figure 14C:
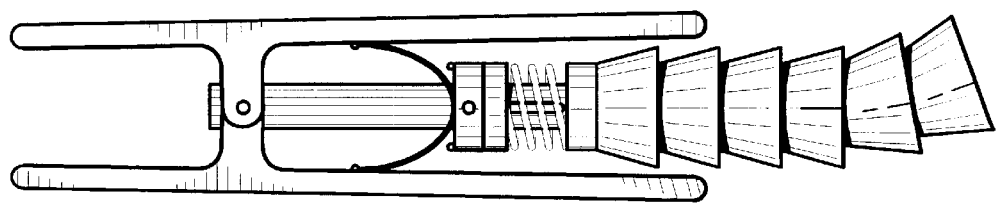
FIG. 14c side view of a fourth bow spring embodiment of the invention in a closed position.

A fourth variation of the bow spring embodiment of the clamp is depicted in FIG. 14. Referring to the side view of FIG. 14b, the clamp 800 of this embodiment includes a first handle 801 and a second handle 802 connected by a center pivot rod 811. A resilient element, not shown for clarity, encircles the center pivot rod 811 and serves to maintain the clamp in a closed position as shown until pressure is applied to the handles 801 and 802. The first handle 801 has an underside 821 that faces an underside 822 of second handle 802.

Connecting the underside 821 of first handle 801 to the underside 822 of second handle 802 is a bow spring 803, fixed at a first end to first anchor point 812 on first handle 801, and fixed at a second end to second anchor point 813 on second handle 802. Attached to the center pivot rod 811 of the clamp is one end of a hollow grooved tube 809. On the other end of the hollow grooved tube 809 opposite of the center pivot rod 811 is a flange or terminating ring 810 that serves as a terminus for the tubular cone-shaped segments 111. Bow spring 803 has an opening 805, depicted in perspective view FIG. 14a, that enables hollow grooved tube to extend through the bow spring 803. A flange 804 on hollow grooved tube 809 serves to limit the backwards flex of bow spring 803 when the clamp 800 is in an open position.

A first sliding ring 807 encircles hollow grooved tube 809, and includes an anchor pin (not shown) that extends laterally through a groove 814 of hollow grooved tube 809. The cable 112 continues through the hollow grooved tube 809 to be attached to the anchor pin of first sliding ring 807. A coil spring 808 serves to separate first sliding ring 807 from terminating ring 810. Disposed on hollow grooved tube 809 between first sliding ring 807 and the bow spring 803 is a second sliding ring 816. In the absence of pressure applied to the handles 810 and 802, there is a space 815 between second sliding ring 816 and first sliding ring 807.

When pressure is applied to the handles 801 and 802, bow spring 803 flexes and comes into contact with the second sliding ring 816, causing it to move so as to close space 815 and engage first sliding ring 807, causing it to slide in groove 814 towards terminating ring 810, compressing spring 808. This releases tension on the cable 112, allowing it to loosen and to make the arm flexible, depicted in FIG. 14c. Release of pressure reverses the process and causes the cable to tighten to make the arm rigid.

As with the case of the coil spring embodiments, there is an embodiment of this bow spring embodiment, depicted in FIG. 15, that utilizes only one sliding ring 807 and thus lacks the space between the first and second sliding rings. In this embodiment, application of pressure to handles 801 and 802 causes bow spring 803 to move sliding ring 807 towards fixed anchor ring 810, compressing coil spring 808, relieving tension on cable 112 thus rendering the arm flexible. However, in this embodiment, since the motion of sliding ring 807 is limited by groove 814 in hollow grooved tube 809, a space can be provided by the backward flex of bow spring 803. Thus, application of pressure to the handles 801 and 802 need not immediately cause the arm to loose rigidity.

Figure 6A:
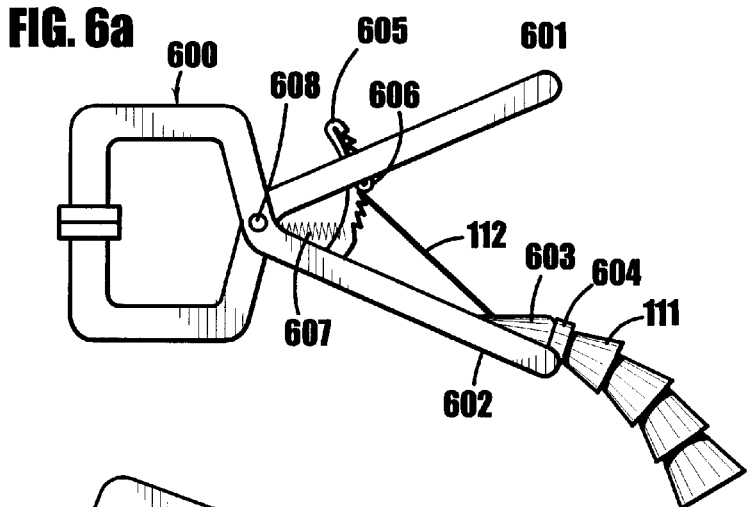
FIG. 6a is a side view of a ratchet type clap embodiment of the invention in a closed position.

FIG. 6a depicts another embodiment of the invention similar to those described that utilizes a ratchet type clamp instead of a spring clamp. This type of clamp uses a scissors mechanism to close and a ratchet mechanism to tighten and hold the clamp in a closed position.

The clamp 600 of this embodiment includes a first handle 601 and a second handle 602 connected by a center pivot rod 608. At the end of second handle 602 is a raised knob 603 attached to a terminating ring 604 that serves as a terminus for the tubular cone-shaped segments 111. Extending upwards from the second handle 602 is a ratchet 605, which extends upwards through an opening in the first handle 601. On the underside of first handle 601 adjacent to the ratchet 605 is a cable roller 606. The cable 112 extends through an opening in terminating ring 604 and a trough in raised knob 603 to run around cable roller 606, terminating at the top end of ratchet 605, where the cable 112 is attached.

Figure 6B:
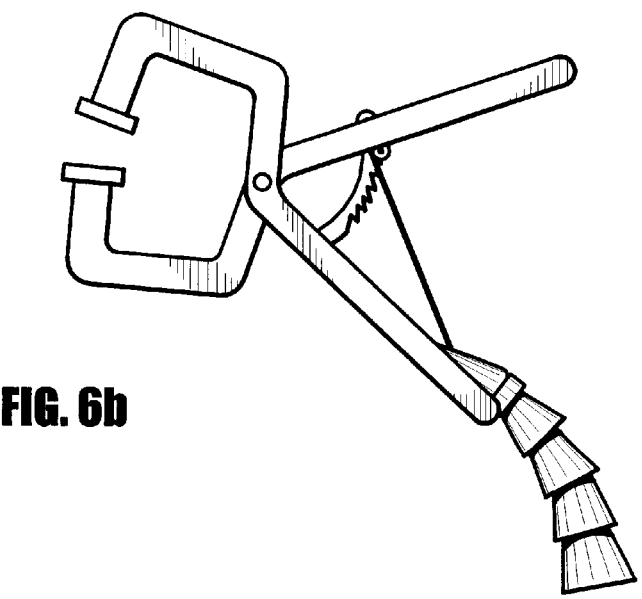
FIG. 6b is a side view of a ratchet type clap embodiment of the invention in an open position.

Whenever the handles 601 and 602 of the clamp 600 are squeezed together to clamp an object, the cable 112 is tightened so as to make the arm rigid. Whenever the ratchet mechanism is released it simultaneously releases the tension on the cable and renders the arm flexible, as shown in FIG. 6b. Whenever the clamp is closed the cable is pulled taut and the arm is made rigid.

The system of the invention is not limited to the embodiments disclosed herein. It will be immediately apparent to those skilled in the art that variations and modifications to the disclosed embodiment are possible without departing from the spirit and scope of the present invention. The invention is defined by the appended claims.

What is claimed is:

1. An apparatus for clamping an object comprising:
   at least one clamp with a first gripping element and a second gripping element, connected by a pivot rod and including a resilient element to maintain the clamp in closed position in the absence of applied pressure; and
   a release mechanism comprising means for maintaining tension in a cable attached to said clamp and said release mechanism when the clamp is in a closed position, and for releasing tension in the cable when the clamp is opened.

2. The apparatus of claim 1, wherein the release mechanism is attached to the second gripping element of the clamp and further comprises:
   a fixed anchor point proximal to the pivot rod;
   a fixed anchor ring with an opening;
   a hollow grooved tube extending from the fixed anchor ring to the fixed anchor point, said hollow grooved tube comprising a groove;
   a first sliding ring to which the cable is attached, said first sliding ring encircling the hollow grooved tube, disposed so that it can slide on the hollow grooved tube;
   a coil spring connecting the first sliding ring to the fixed anchor ring;
   a second sliding ring encircling the hollow grooved tube, disposed so that it can slide on the hollow grooved tube between the first sliding ring and the fixed anchor point; and
   a lever arm connecting the second sliding ring to the first gripping element,
   wherein, in the absence of pressure, the coil spring serves to maintain tension on the cable so as to render the arm rigid, and wherein application of pressure to the clamp gripping elements causes the lever arm to move second sliding ring into contact with the first sliding ring so as to compress the spring and relieve tension on the cable, causing the arm to become flexible.

3. The apparatus of claim 2, wherein the first sliding ring further comprises an anchor pin disposed on the inside of the first sliding ring that extends through the groove of the hollow grooved tube and to which the cable is attached.

4. The apparatus of claim 1, wherein the release mechanism is positioned between the first and second gripping elements and further comprises:
   a hollow grooved tube extending from the pivot rod to the arm, and terminating with a raised anchor ring, said hollow grooved tube comprising a groove;
   a first sliding ring to which the cable attaches, said first sliding ring encircling the hollow grooved tube, disposed so that it can slide on the hollow grooved tube;
   a coil spring connecting the sliding ring to the raised anchor ring;
   a second sliding ring encircling the hollow grooved tube, disposed so that it can slide on the hollow grooved tube between the first sliding ring and the pivot rod;
   a first lever arm connecting the second sliding ring to the first gripping element; and
   a second lever arm connecting the second sliding ring to the second gripping element,
   wherein, in the absence of pressure, the coil spring serves to maintain tension on the cable so as to render the arm rigid, and wherein application of pressure to the clamp gripping elements causes the first and second lever arms to move the second sliding ring into contact with the first sliding ring so as to compress the spring and relieve tension on the cable, causing the arm to become flexible.

5. The apparatus of claim 4, wherein the sliding ring further comprises an anchor pin disposed on the inside of the sliding ring that extends through the groove of the hollow, grooved tube and to which the cable is attached.

6. The apparatus of claim 1, wherein the release mechanism is positioned between the first and second gripping elements and further comprises:
   a hollow grooved tube extending from the pivot rod to the arm, and terminating with a raised anchor ring, said hollow grooved tube comprising a groove;
   a first sliding ring to which the cable attaches, said first sliding ring encircling the hollow grooved tube, disposed so that it can slide on the hollow grooved tube;
   a coil spring connecting the sliding ring to the raised anchor ring;
   a second sliding ring encircling the hollow grooved tube, disposed so that it can slide on the hollow grooved tube between the first sliding ring and the pivot rod; and
   a horseshoe lever arm connecting the second sliding ring to one of said first or second gripping elements,
   wherein, in the absence of pressure, the coil spring serves to maintain tension on the cable so as to render the arm rigid, and wherein application of pressure to the clamp gripping elements causes the horseshoe lever arm to move the second sliding ring into contact with the first sliding ring so as to compress the spring and relieve tension on the cable, causing the arm to become flexible.

7. The apparatus of claim 6, wherein the sliding ring further comprises an anchor pin disposed on the inside of the sliding ring that extends through the groove of the hollow, grooved tube and to which the cable is attached.

8. The apparatus of claim 1, wherein the second gripping element includes a raised knob at an end opposite from the pivot rod, said raised knob including a bore through which the cable can pass, and wherein the release mechanism is positioned on the first and second gripping elements and further comprises:

a first bow spring with two ends and fixed at both ends to the first gripping element;

a second bow spring attached to said second gripping element so as to face the first bow spring fixed to the first gripping element, said second bow spring being fixed at a first end proximal to the pivot rod; and a third bow spring attached to said second gripping element between said second bow spring and said raised knob, wherein a first end of said third bow spring is fixed proximal to said raised knob, and wherein a second end of said third bow spring is attached to the second end of second bow spring by a sliding connection, said third bow spring including a groove through which the cable can pass, and an anchor point proximal to its second end to which the cable can attach, wherein, in the absence of pressure, the third bow spring maintains tension on the cable so as to render the arm rigid, and wherein application of pressure to the clamp gripping elements causes the first bow spring to depress the second bow spring so as to move the sliding connection towards the raised know and to compress third bow spring so as relieve tension on the cable, causing the arm to become flexible.

9. The apparatus of claim 8, wherein the second gripping element further comprises a recessed track in which the sliding connection can move.

10. The apparatus of claim 1, wherein the release mechanism comprises:

a first bow spring fixed to the first gripping element;

a second bow spring fixed to the second gripping element;

a hollow grooved tube connecting the pivot rod to the arm, and terminating with a raised anchor ring;

a sliding ring to which the cable attaches, said sliding ring encircling the hollow, grooved tube, disposed so that it can slide on the hollow grooved tube;

a coil spring connecting the sliding ring to the raised anchor ring;

a first flexible bow spring attached to said hollow grooved tube so as to face said first bow spring, wherein a first end of said first flexible bow spring is fixed proximal to said pivot rod, and wherein a second end of said first flexible bow spring is attached to the sliding ring; and a second flexible bow spring attached to said hollow grooved tube so as to face said second bow spring, wherein a first end of said second flexible bow spring is fixed proximal to said pivot rod, and wherein a second end of said second flexible bow spring is attached to the sliding ring, wherein, in the absence of pressure, the coil spring maintains tension on the cable so as to render the arm rigid, and wherein application of pressure to the clamp gripping elements causes the first bow spring to depress the first flexible bow spring and the second bow spring to depress the second flexible bow spring so as to move the sliding ring towards the anchor ring and to compress the coil spring so as relieve tension on the cable, causing the arm to become flexible.

11. The apparatus of claim 10, wherein the first sliding ring further comprises an anchor pin disposed on the inside of the sliding ring that extends through the groove of the hollow, grooved tube and to which the cable is attached.

12. The apparatus of claim 1, wherein the release mechanism comprises:

a first bow spring fixed to the first gripping element;

a second bow spring fixed to the second gripping element;

a hollow grooved tube connecting the pivot rod to the arm, and terminating with a raised anchor ring;

a first sliding ring to which the cable attaches, said sliding ring encircling the hollow, grooved tube, disposed so that it can slide on the hollow grooved tube;

a coil spring connecting the sliding ring to the raised anchor ring;

a second sliding ring encircling the hollow grooved tube, disposed so that it can slide between the first sliding ring and the pivot rod;

a first flexible bow spring attached to said hollow grooved tube so as to face said first bow spring, wherein a first end of said first flexible bow spring is fixed proximal to said pivot rod, and wherein a second end of said first flexible bow spring is attached to the second sliding ring; and a second flexible bow spring attached to said hollow grooved tube so as to face said second bow spring, wherein a first end of said second flexible bow spring is fixed proximal to said pivot rod, and wherein a second end of said second flexible bow spring is attached to the second sliding ring, wherein, in the absence of pressure, the coil spring maintains tension on the cable so as to render the arm rigid, and wherein application of pressure to the clamp gripping elements causes the first bow spring to depress the first flexible bow spring and the second bow spring to depress the second flexible bow spring so as to move the second sliding ring into contact with first sliding ring, moving first sliding ring towards the anchor ring and compressing the coil spring so as relieve tension on the cable, causing the arm to become flexible.

13. The apparatus of claim 12, wherein the first sliding ring further comprises an anchor pin disposed on the inside of the sliding ring that extends through the groove of the hollow, grooved tube and to which the cable is attached.

14. The apparatus of claim 1, wherein the release mechanism comprises:

a hollow grooved tube connecting the pivot rod to the arm, and terminating with a raised anchor ring;

a bow spring fixed to the first gripping element and the second gripping element, comprising an opening through which the hollow grooved tube can extend;

a first sliding ring to which the cable attaches, said sliding ring encircling the hollow, grooved tube, disposed so that it can slide on the hollow grooved tube;

a coil spring connecting the sliding ring to the raised anchor ring; and a second sliding ring encircling the hollow grooved tube, disposed so that it can slide between the first sliding ring and the bow spring, wherein, in the absence of pressure, the coil spring maintains tension on the cable so as to render the arm rigid, and wherein application of pressure to the clamp gripping elements causes the bow spring to flex towards the second sliding ring so as to move the second sliding ring into contact with first sliding ring, moving first sliding ring towards the anchor ring and compressing the coil spring so as relieve tension on the cable, causing the arm to become flexible.

15. The apparatus of claim 14, wherein the first sliding ring further comprises an anchor pin disposed on the inside of the sliding ring that extends through the groove of the hollow, grooved tube and to which the cable is attached, and wherein the hollow grooved tube further comprises a flange disposed proximal to the pivot rod so as to limit a backwards flex of the bow spring.

16. The apparatus of claim 1, wherein the first and second gripping elements are connected via a scissors type of connection and wherein the release mechanism comprises:

a raised knob fixed to an end of said second arm opposite from said pivot rod, said raised knob having an opening through the cable can pass and serving as a terminus for the arm;

a ratchet arm attached to said second gripping element between the raised knob and the pivot rod and extending upward from said second gripping element past said first gripping element; and a cable roller fixed to said first gripping element on a side facing where said ratchet is attached to said second gripping element and adjacent to where said ratchet passes said first gripping element, wherein said cable extends from said raised knob past said cable roller to an end of said ratchet to which the cable is fixed, and wherein said spring maintains said clamp in a closed position in the absence of pressure on the clamp gripping elements and maintains tension on the cable rendering the arm rigid, and applying pressure to pull the gripping elements apart releases tension on the cable rendering the arm flexible.

17. The apparatus of claim 1, wherein the release mechanism is positioned between the first and second gripping elements and further comprises:

a hollow grooved tube extending from the pivot rod to the arm, and terminating with a raised anchor ring, said hollow grooved tube comprising a groove;

a sliding ring to which the cable attaches, said sliding ring encircling the hollow grooved tube, disposed so that it can slide on the hollow grooved tube;

a coil spring connecting the sliding ring to the raised anchor ring;

a first lever arm connecting the sliding ring to the first gripping element; and a second lever arm connecting the sliding ring to the second gripping element, wherein, in the absence of pressure, the coil spring serves to maintain tension on the cable so as to render the arm rigid, and wherein application of pressure to the clamp gripping elements causes the first and second lever arms to move the sliding ring so as to compress the spring and relieve tension on the cable, causing the arm to become flexible.

18. The apparatus of claim 17, wherein the sliding ring further comprises an anchor pin disposed on the inside of the sliding ring that extends through the groove of the hollow grooved tube and to which the cable is attached.

19. The apparatus of claim 1, wherein the release mechanism is attached to the second gripping element of the clamp and further comprises:

a fixed anchor point proximal to the pivot rod;

a fixed anchor ring with an opening;

a hollow grooved tube extending from the fixed anchor ring to the fixed anchor point, said hollow grooved tube comprising a groove;

a sliding ring to which the cable is attached, said sliding ring encircling the hollow grooved tube, disposed so that it can slide on the hollow grooved tube;

a coil spring connecting the sliding ring to the fixed anchor ring; and a lever arm connecting the sliding ring to the first gripping element, wherein, in the absence of pressure, the coil spring serves to maintain tension on the cable so as to render the arm rigid, and wherein application of pressure to the clamp gripping elements causes the lever arm to move the sliding ring so as to compress the spring and relieve tension on the cable, causing the arm to become flexible.

20. The apparatus of claim 19, wherein the sliding ring further comprises an anchor pin disposed on the inside of the first sliding ring that extends through the groove of the hollow grooved tube and to which the cable is attached.

21. The apparatus of claim 1, wherein the release mechanism comprises:

a hollow grooved tube connecting the pivot rod to the arm, and terminating with a raised anchor ring;

a bow spring fixed to the first gripping element and the second gripping element, comprising an opening through which the hollow grooved tube can extend;

a sliding ring to which the cable attaches, said sliding ring encircling the hollow, grooved tube, disposed so that it can slide on the hollow grooved tube; and a coil spring connecting the sliding ring to the raised anchor ring, wherein, in the absence of pressure, the coil spring maintains tension on the cable so as to render the arm rigid, and wherein application of pressure to the clamp gripping elements causes the bow spring to flex towards the sliding ring so as to move the sliding ring and compress the coil spring so as relieve tension on the cable, causing the arm to become flexible.

22. The apparatus of claim 21, wherein the sliding ring further comprises an anchor pin disposed on the inside of the sliding ring that extends through the groove of the hollow, grooved tube and to which the cable is attached, and wherein the hollow grooved tube further comprises a flange disposed proximal to the pivot rod so as to limit a backwards flex of the bow spring.

23. The apparatus of claim 1, further comprising at least one arm comprising a flexible casing that encases the cable.

24. The apparatus of claim 23, wherein the flexible casing comprises a plurality of tubular, cone shaped segments.

25. The apparatus of claim 24, wherein the tubular cone shaped segments are open at a wide end and closed at a narrow end, and wherein the narrow end is penetrated by a bore through which the cable can pass.

26. The apparatus of claim 23, further comprising a central anchor point to which one end of the at least one arm terminates, said central anchor point further comprising a cylindrical section and a toggle means to which said cable attaches, a first end of said toggle means being hingedly attached to said cylindrical section, wherein when said toggle means is in a locked position the cable is under tension, rendering the arm rigid, and when said toggle means is in an unlocked position, tension in the cable is released rendering the arm flexible.

27. The apparatus of claim 26, wherein the toggle means is held in the locked position by a spring disposed between said toggle means and said cylindrical section, and wherein said toggle means is depressed into the unlocked position.

28. The apparatus of claim 26, wherein the toggle means includes a protuberance proximal to the first end, and the cylindrical section includes a depression disposed to receive the protuberance when the toggle means is in the locked position, said depression shaped to hold the toggle means in the locked position until the toggle means is moved to the unlocked position.

29. The apparatus of claim 26, further comprising a plurality of clamps and a plurality of arms, each said clamp being connected to the central anchor point by one of said arms, each arm encasing a cable that connects from the clamp to the central anchor point, the central anchor point further comprising a plurality of toggle means so that each said cable connects to one of the plurality of toggle means.

30. An apparatus for clamping an object comprising:
   a clamp with a first gripping element and a second gripping element, connected by a pivot rod with a resilient element to maintain the clamp in closed position in the absence of applied pressure;
   an arm comprising a cable encased by a plurality of tubular, cone shaped segments, each said tubular cone shaped segment being open at a wide end and closed at a narrow end, said closed end being penetrated by a bore through which the cable can pass; and
   a release mechanism attached to the second gripping element, said cable attaching to said release mechanism, wherein said release mechanism further comprises:
      a fixed anchor point proximal to the pivot rod;
      a fixed anchor ring with an opening;
      a hollow grooved tube extending from the fixed anchor ring to the fixed anchor point;
      a first sliding ring with an anchor pin to which the cable is attached, said first sliding ring encircling the hollow, grooved tube, disposed so that it can slide on the hollow grooved tube;
      a coil spring connecting the first sliding ring to the fixed anchor ring;
      a second sliding ring encircling the hollow, grooved tube, disposed so that it can slide on the hollow grooved tube between the first sliding ring and the fixed anchor point; and
      a lever arm connecting the second sliding ring to the first gripping element,
   wherein, in the absence or pressure, the coil spring serves to maintain tension on the cable so as to render the arm rigid, and wherein application of pressure to the clamp gripping elements causes the lever arm to move second sliding ring into contact with the first sliding ring so as to compress the spring and relieve tension on the cable, causing the arm to become flexible.

31. An apparatus for clamping an object comprising:
   a clamp with a first gripping element and a second gripping element, connected by a pivot rod with a resilient element to maintain the clamp in closed position in the absence of applied pressure;
   an arm comprising a cable encased by a plurality of tubular, cone shaped segments, each said tubular cone shaped segment being open at a wide end and closed at a narrow end, said closed end being penetrated by a bore through which the cable can pass; and
   a release mechanism positioned between the first and second gripping elements that further comprises:
      a hollow grooved tube extending from the pivot rod to the arm, and terminating with a raised anchor ring;
      a first sliding ring to which the cable attaches, said first sliding ring encircling the hollow, grooved tube, disposed so that it can slide on the hollow grooved tube;
      a coil spring connecting the sliding ring to the raised anchor ring;
      a second sliding ring encircling the hollow, grooved tube, disposed so that it can slide on the hollow grooved tube between the first sliding ring and the pivot rod;
      a first lever arm connecting the second sliding ring to the first gripping element; and
      a second lever arm connecting the second sliding ring to the second gripping element,
   wherein, in the absence of pressure, the coil spring serves to maintain tension on the cable so as to render the arm rigid, and wherein application of pressure to the clamp gripping elements causes the first and second lever arms to move the second sliding ring into contact with the first sliding ring so as to compress the spring and relieve tension on the cable, causing the arm to become flexible.

32. An apparatus for clamping an object comprising:
   an arm comprising a cable encased by a plurality of tubular, cone shaped segments, each said tubular cone shaped segment being open at a wide end and closed at a narrow end, said closed end being penetrated by a bore through which the cable can pass;
   a clamp with a first gripping element and a second gripping element, connected by a pivot rod with a resilient element to maintain the clamp in closed position in the absence of applied pressure, wherein the second gripping element includes a raised knob at an end opposite from the pivot rod, said raised knob including a bore through which the cable can pass; and
   a release mechanism positioned on the first and second gripping elements that comprises:
      a first bow spring with two ends and fixed at both ends to the first gripping element;
      a second bow spring attached to said second gripping element so as to face the first bow spring fixed to the first gripping element, said second bow spring being fixed at a first end proximal to the pivot rod; and
      a third bow spring attached to said second gripping element between said second bow spring and said raised knob, wherein a first end of said third bow spring is fixed proximal to said raised knob, and wherein a second end of said third bow spring is attached to the second end of second bow spring by a sliding connection, said third bow spring including a groove through which the cable can pass, and an anchor point proximal to its second end to which the cable can attach,
   wherein, in the absence of pressure, the third bow spring maintains tension on the cable so as to render the arm rigid, and wherein application of pressure to the clamp gripping elements causes the first bow spring to depress the second bow spring so as to move the sliding connection towards the raised know and to compress third bow spring so as relieve tension on the cable, causing the arm to become flexible.

33. An apparatus for clamping an object comprising:
   a clamp with a first gripping element and a second gripping element, connected by a pivot rod with a resilient element to maintain the clamp in closed position in the absence of applied pressure;
   an arm comprising a cable encased by a plurality of tubular, cone shaped segments, each said tubular cone shaped segment being open at a wide end and closed at a narrow end, said closed end being penetrated by a bore through which the cable can pass; and a release mechanism that comprises:
- a first bow spring fixed to the first gripping element;
- a second bow spring fixed to the second gripping element;
- a hollow grooved tube connecting the pivot rod to the arm, and terminating with a raised anchor ring;
- a sliding ring to which the cable attaches, said sliding ring encircling the hollow, grooved tube, disposed so that it can slide on the hollow grooved tube;
- a coil spring connecting the sliding ring to the raised anchor ring;
- a first flexible bow spring attached to said hollow grooved tube so as to face said first bow spring, wherein a first end of said first flexible bow spring is fixed proximal to said pivot rod, and wherein a second end of said first flexible bow spring is attached to the sliding ring; and
- a second flexible bow spring attached to said hollow grooved tube so as to face said second bow spring, wherein a first end of said second flexible bow spring is fixed proximal to said pivot rod, and wherein a second end of said second flexible bow spring is attached to the sliding ring, wherein, in the absence of pressure, the coil spring maintains tension on the cable so as to render the arm rigid, and wherein application of pressure to the clamp gripping elements causes the first bow spring to depress the first flexible bow spring and the second bow spring to depress the second flexible bow spring so as to move the sliding ring towards the anchor ring and to compress the coil spring so as relieve tension on the cable, causing the arm to become flexible.

34. An apparatus for clamping an object comprising:

a clamp with a first gripping element and a second gripping element, connected by a pivot rod and including a resilient element to maintain the clamp in closed position in the absence of applied pressure, wherein the first and second gripping elements are connected via a scissors type of connection;

an arm comprising a cable encased by a plurality of tubular, cone shaped segments, each said tubular cone shaped segment being open at a wide end and closed at a narrow end, said closed end being penetrated by a bore through which the cable can pass; and a release mechanism comprising:
- a raised knob fixed to an end of said second arm opposite from said pivot rod, said raised knob having an opening through the cable can pass and serving as a terminus for the arm;
- a ratchet arm attached to said second gripping element between the raised knob and the pivot rod and extending upward from said second gripping element past said first gripping element; and
- a cable roller fixed to said first gripping element on a side facing where said ratchet is attached to said second gripping element and adjacent to where said ratchet passes said first gripping element, wherein said cable extends from said raised knob past said cable roller to an end of said ratchet to which the cable is fixed, and wherein said spring maintains said clamp in a closed position in the absence of pressure on the clamp gripping elements and maintains tension on the cable rendering the arm rigid, and applying pressure to pull the gripping elements apart releases tension on the cable rendering the arm flexible.

35. An apparatus for clamping an object comprising:

a clamp with a first gripping element and a second gripping element, connected by a pivot rod with a resilient element to maintain the clamp in closed position in the absence of applied pressure;

an arm comprising a cable encased by a plurality of tubular, cone shaped segments, each said tubular cone shaped segment being open at a wide end and closed at a narrow end, said closed end being penetrated by a bore through which the cable can pass; and a release mechanism comprising:
- a first bow spring fixed to the first gripping element;
- a second bow spring fixed to the second gripping element;
- a hollow grooved tube connecting the pivot rod to the arm, and terminating with a raised anchor ring;
- a first sliding ring to which the cable attaches, said sliding ring encircling the hollow, grooved tube, disposed so that it can slide on the hollow grooved tube;
- a coil spring connecting the sliding ring to the raised anchor ring;
- a second sliding ring encircling the hollow grooved tube, disposed so that it can slide between the first sliding ring and the pivot rod;
- a first flexible bow spring attached to said hollow grooved tube so as to face said first bow spring, wherein a first end of said first flexible bow spring is fixed proximal to said pivot rod, and wherein a second end of said first flexible bow spring is attached to the second sliding ring; and
- a second flexible bow spring attached to said hollow grooved tube so as to face said second bow spring, wherein a first end of said second flexible bow spring is fixed proximal to said pivot rod, and wherein a second end of said second flexible bow spring is attached to the second sliding ring, wherein, in the absence of pressure, the coil spring maintains tension on the cable so as to render the arm rigid, and wherein application of pressure to the clamp gripping elements causes the first bow spring to depress the first flexible bow spring and the second bow spring to depress the second flexible bow spring so as to move the second sliding ring into contact with first sliding ring, moving first sliding ring towards the anchor ring and compressing the coil spring so as relieve tension on the cable, causing the arm to become flexible.

36. An apparatus for clamping an object comprising:

a clamp with a first gripping element and a second gripping element, connected by a pivot rod with a resilient element to maintain the clamp in closed position in the absence of applied pressure;

an arm comprising a cable encased by a plurality of tubular, cone shaped segments, each said tubular cone shaped segment being open at a wide end and closed at a narrow end, said closed end being penetrated by a bore through which the cable can pass; and a release mechanism comprising:
- a hollow grooved tube connecting the pivot rod to the arm, and terminating with a raised anchor ring;
- a bow spring fixed to the first gripping element and the second gripping element, comprising an opening through which the hollow grooved tube can extend;
- a first sliding ring to which the cable attaches, said sliding ring encircling the hollow, grooved tube, disposed so that it can slide on the hollow grooved tube;

a coil spring connecting the sliding ring to the raised anchor ring; and a second sliding ring encircling the hollow grooved tube, disposed so that it can slide between the first sliding ring and the bow spring, wherein, in the absence of pressure, the coil spring maintains tension on the cable so as to render the arm rigid, and wherein application of pressure to the clamp gripping elements causes the bow spring to flex towards the second sliding ring so as to move the second sliding ring into contact with first sliding ring, moving first sliding ring towards the anchor ring and compressing the coil spring so as relieve tension on the cable, causing the arm to become flexible.

37. The apparatus of one of claims 30, 31, 32, 33, 34, 35 or 36, further comprising a central anchor point to which one end of the arm terminates, said central anchor point further comprising a cylindrical section and a toggle means to which said cable attaches, a first end of said toggle means being hingedly attached to said cylindrical section, wherein when said toggle means is in a locked position the cable is under tension, rendering the arm rigid, and when said toggle means is in an unlocked position, tension in the cable is released rendering the arm flexible.

38. The apparatus of claim 37, wherein the toggle arm is held in the locked position by a spring disposed between said toggle arm and said cylindrical section, and wherein said toggle arm is depressed into the unlocked position.

39. The apparatus of claim 37, wherein the toggle arm includes a protuberance proximal to the first end, and the cylindrical section includes a depression disposed to receive the protuberance when the toggle is in the locked position, said depression shaped to hold the toggle arm in the locked position until the toggle arm is moved to the unlocked position.

40. The apparatus of claim 37, further comprising a plurality of clamps and a plurality of arms, each said clamp being connected to the central anchor point by one of said arms, each arm encasing a cable that connects from the clamp to the central anchor point, the central anchor point further comprising a plurality of toggle means so that each said cable connects to one of the plurality of toggle means.

* * * * *